US008801656B2

(12) United States Patent
Lowery et al.

(10) Patent No.: US 8,801,656 B2
(45) Date of Patent: Aug. 12, 2014

(54) FLUID FLOW PASSAGE TO IMPROVE AIR-IN-LINE DETECTION

(71) Applicants: Michael G. Lowery, Wildwood, IL (US); Tamas Ban, Grayslake, IL (US); Anatoly S. Belkin, Glenview, IL (US); Paul T. Kotnik, Commerce Township, MI (US)

(72) Inventors: Michael G. Lowery, Wildwood, IL (US); Tamas Ban, Grayslake, IL (US); Anatoly S. Belkin, Glenview, IL (US); Paul T. Kotnik, Commerce Township, MI (US)

(73) Assignee: Hospira, Inc., Lake Forest, IL (US)

( * ) Notice: Subject to any disclaimer, the term of this patent is extended or adjusted under 35 U.S.C. 154(b) by 0 days.

(21) Appl. No.: 14/065,938

(22) Filed: Oct. 29, 2013

(65) Prior Publication Data

US 2014/0121639 A1     May 1, 2014

Related U.S. Application Data

(60) Provisional application No. 61/719,739, filed on Oct. 29, 2012.

(51) Int. Cl.
*A61M 31/00*     (2006.01)
*A61M 5/168*     (2006.01)
*A61M 5/142*     (2006.01)
*A61M 5/36*     (2006.01)
*A61M 5/172*     (2006.01)

(52) U.S. Cl.
CPC ............ *A61M 5/36* (2013.01); *A61M 5/16831* (2013.01); *A61M 5/142* (2013.01); *A61M 5/172* (2013.01)
USPC ............................. 604/65; 604/67; 73/861.63

(58) Field of Classification Search
CPC ..... A61M 5/36; A61M 5/16831; A61M 5/172
USPC .......................... 73/861.63, 861.04; 600/459; 604/65–67, 253
See application file for complete search history.

(56) References Cited

U.S. PATENT DOCUMENTS

| | | |
|---|---|---|
| 1,248,058 A | 11/1917 | Bailey |
| 3,898,637 A | 8/1975 | Wolstenholme |
| 3,913,384 A | 10/1975 | Furuya et al. |
| 3,921,622 A | 11/1975 | Cole |
| 4,068,521 A | 1/1978 | Cosentino et al. |
| 4,213,454 A | 7/1980 | Shim |
| 4,291,701 A | 9/1981 | Bowman et al. |
| 4,381,591 A | 5/1983 | Barger et al. |
| 4,397,648 A | 8/1983 | Knute et al. |
| 4,418,565 A | 12/1983 | St. John |

(Continued)

FOREIGN PATENT DOCUMENTS

WO     9116087     10/1991

OTHER PUBLICATIONS

Stegmayr et al., Development of air micro bubbles in the venous outlet line: an in vitro analysis of various air traps used for hemodialysis; Artif Organs. Jun. 2007, 483-8, 31(6).

(Continued)

*Primary Examiner* — Nicholas Lucchesi
*Assistant Examiner* — Gerald Landry, II
(74) *Attorney, Agent, or Firm* — Michael R. Crabb

(57) ABSTRACT

Infusion systems and methods containing unique inner passage configurations are provided to improve the in-line detection of air in a fluid delivery line of an infusion system by reducing the problems associated with the presence of bouncing air bubbles and stuck fluid droplets in the fluid delivery line.

20 Claims, 8 Drawing Sheets

(56) References Cited

U.S. PATENT DOCUMENTS

| | | | |
|---|---|---|---|
| 4,528,847 | A | 7/1985 | Halmi et al. |
| 4,551,134 | A | 11/1985 | Slavik et al. |
| 4,607,520 | A | 8/1986 | Dam et al. |
| 4,722,725 | A | 2/1988 | Sawyer |
| 4,881,413 | A | 11/1989 | Georgi et al. |
| 5,031,465 | A | 7/1991 | Redus |
| 5,102,392 | A | 4/1992 | Sakai et al. |
| 5,154,513 | A | 10/1992 | Beer et al. |
| 5,177,993 | A | 1/1993 | Beckman et al. |
| 5,205,153 | A | 4/1993 | Hlavinka et al. |
| 5,421,209 | A | 6/1995 | Redus et al. |
| 5,489,265 | A | 2/1996 | Montalvo et al. |
| 5,515,713 | A | 5/1996 | Saugues et al. |
| 5,524,475 | A | 6/1996 | Kolpak et al. |
| 5,658,133 | A | 8/1997 | Anderson et al. |
| 5,693,891 | A | 12/1997 | Brown et al. |
| 5,723,773 | A * | 3/1998 | Bryan .................. 73/61.75 |
| 5,736,650 | A * | 4/1998 | Hiron et al. ............ 73/861.63 |
| 5,793,216 | A * | 8/1998 | Constant ............... 324/639 |
| 6,085,574 | A | 7/2000 | Neftel et al. |
| 6,221,065 | B1 * | 4/2001 | Davis .................. 604/539 |
| 6,290,681 | B1 | 9/2001 | Brown et al. |
| 6,489,896 | B1 | 12/2002 | Platt |
| 6,515,487 | B1 | 2/2003 | Dawson |
| 6,755,086 | B2 | 6/2004 | Salamitou |
| 6,935,189 | B2 * | 8/2005 | Richards .............. 73/861.04 |
| 7,190,275 | B2 | 3/2007 | Goldberg et al. |
| 7,377,148 | B2 | 5/2008 | Cassidy et al. |
| 7,707,897 | B2 * | 5/2010 | Ong .................... 73/861.04 |
| 7,810,401 | B2 | 10/2010 | Brown et al. |
| 7,866,201 | B1 | 1/2011 | Tutu et al. |
| 7,998,115 | B2 | 8/2011 | Bedingfield |
| 8,033,157 | B2 * | 10/2011 | Yardimci et al. ........ 73/19.01 |
| 8,061,219 | B2 * | 11/2011 | Rezgui et al. .......... 73/861.63 |
| 8,105,269 | B2 | 1/2012 | Zhou et al. |
| 2004/0025597 | A1 | 2/2004 | Ericson |
| 2008/0077073 | A1 * | 3/2008 | Keenan et al. ............ 604/19 |
| 2009/0157040 | A1 | 6/2009 | Jacobson et al. |
| 2011/0106462 | A1 * | 5/2011 | Kilburn et al. ........... 702/47 |
| 2012/0206128 | A1 * | 8/2012 | Marshall et al. ......... 324/149 |
| 2012/0245554 | A1 | 9/2012 | Kawamura |

OTHER PUBLICATIONS

Kutschka et al, A new minimized perfusion circuit provides highly effective ultrasound controlled deairing; Artif Organs. Mar. 2007, 215-20, 31(3).

Palanchon et al., Acoustical Bubble Trapper Applied to Hemodialysis, Ultrasound in Med. & Biol., Apr. 2008, pp. 681-684, vol. 34, No. 4.

\* cited by examiner

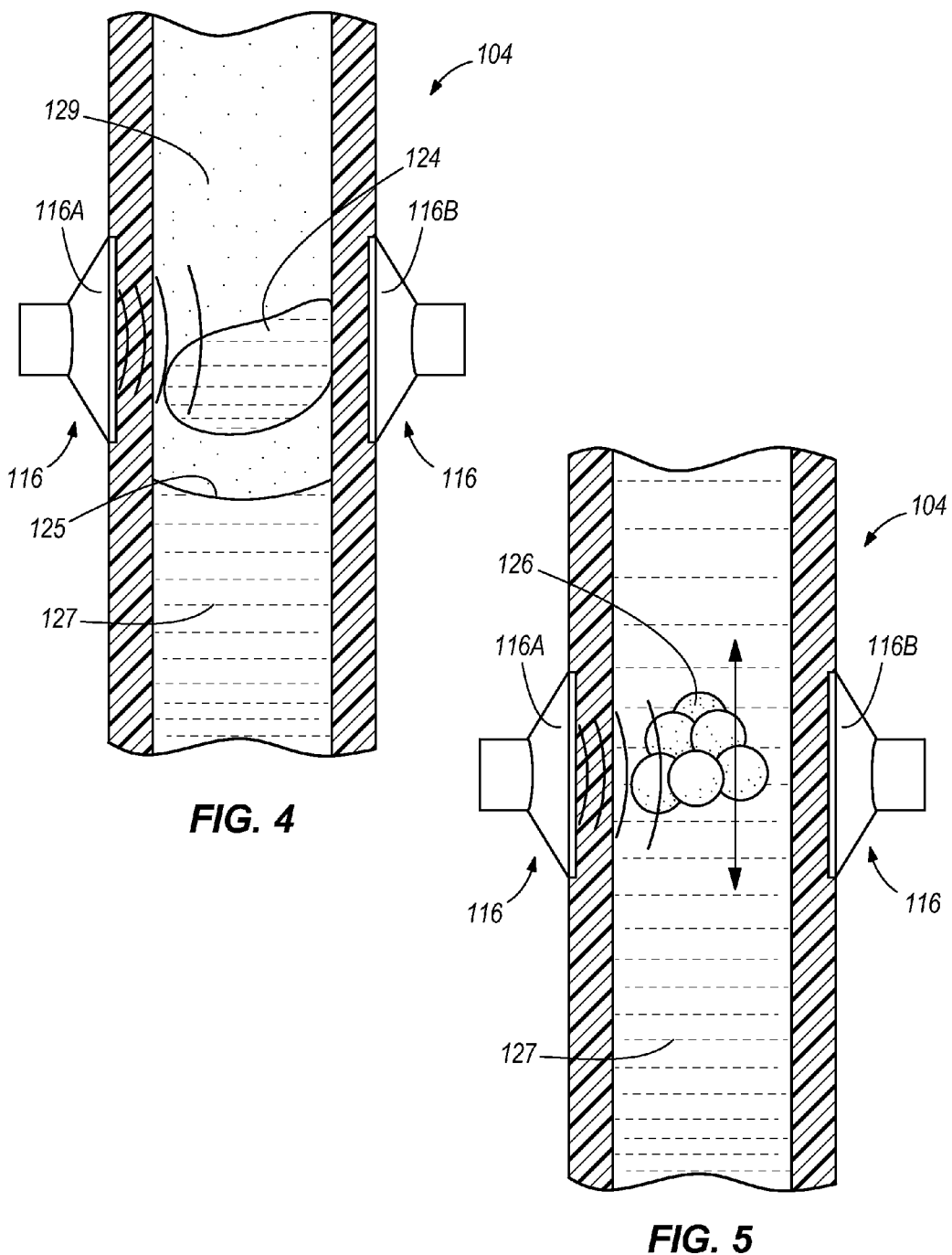

FLUID FLOW PASSAGE TO IMPROVE AIR-IN-LINE DETECTION

FIELD OF THE DISCLOSURE

The present invention relates to a system and method for improving the in-line detection of air in a fluid delivery line of an infusion system by reducing the problems associated with the presence of bouncing air bubbles or stuck fluid droplets in the fluid delivery line by providing unique configurations of the fluid delivery line.

BACKGROUND OF THE DISCLOSURE

Ultrasonic transducer pairs, comprising a transmitter and a receiver, are commonly applied to detect air in a fluid delivery line segment as part of medication infusion systems, such as Plum A+™, Gemstar™ and Symbig™. The sensors are physically located on opposite sides of a fluid delivery line segment and the presence of air in the fluid delivery line causes an acoustical open circuit which substantially attenuates the detected signal. When fluid is present, propagation of the acoustic signal is efficient and produces a large electrical signal via the receiver circuit.

Detection of air in the fluid delivery line segment is typically performed on the basis of a fixed air-fluid boundary or threshold that is applied to the sensor voltage or current signal. Any signal on the fluid side of the threshold is classified as representing the presence of fluid in the infusion line and any signal on the air side of the threshold is classified as representing air. Typically a fixed threshold is applied that is specific to the infusion pump set and sensor arrangement.

When oscillating (bouncing) air bubbles are present in the fluid delivery line segment at the sensors of the infusion system, false air-in-line alarms may occur, due to the oscillating air bubbles continuously bouncing around the sensors thereby being repetitively counted and misleading the clinician into believing that the total air volume within the fluid delivery line has exceeded a total air threshold. This may cause the clinician to constantly stop the infusion system when it is not necessary.

When air is infused in the fluid delivery line segment past the sensors, the presence of a stationary fluid droplet (stuck fluid droplet) that bridges the gap between the sensors may lead to an acoustic short circuit. This can produce an absolute sensor signal similar to that of a fluid and result in a false negative indicating the presence of fluid when air is actually disposed over the sensor. This is problematic because the air sensor signal, indicating that air is in the infusion line, is typically used to produce an air-in-line alarm to pause the pumping mechanism and to reduce the potential for the infusion of air into a patient's vascular system. When a stuck fluid droplet is present at the sensors, the sensors may detect that fluid is present and as a result the air-in-line alarm may not be triggered even though air may be disposed in the fluid delivery line. This may create health issues for the patient.

Some infusion systems and methods have attempted to resolve the issues associated with bouncing air bubbles and stationary fluid droplets by developing complex algorithms to attempt to account for every potential situation in order to determine when air is in the system. However, it is virtually impossible to account for every situation through an algorithm alone.

An infusion system and method is needed which will improve the in-line detection of air in a fluid delivery line of an infusion system by reducing the problems associated with the presence of bouncing air bubbles and stuck fluid droplets in the fluid delivery line.

SUMMARY OF THE DISCLOSURE

In one embodiment of the disclosure, an infusion system includes at least one sensor, and a fluid delivery line having an inner passage extending longitudinally within the fluid delivery line. The inner passage includes: an upstream portion; a downstream portion; and an orifice connecting the upstream portion to the downstream portion. The infusion system further includes: (1) a pump with at least one sensor being disposed at the upstream portion, the orifice having an orifice inner diameter of 0.508 millimeters (0.020 inches) or smaller, and the upstream portion having a first volume which is at least 25 percent smaller than a second volume of fluid delivered by a stroke of the pump; (2) at least one sensor disposed at the upstream portion, the orifice having an orifice inner diameter of 0.508 millimeters (0.020 inches) or smaller, and an upstream portion inner diameter of the upstream portion being 2.286 millimeters (0.090 inches) or larger; (3) at least one sensor disposed at the downstream portion, and the downstream portion having a downstream portion inner diameter of 0.508 millimeters (0.020 inches) or smaller; or (4) at least one sensor disposed at the upstream portion, and a cross-section of the upstream portion having an elliptical shape or a prolate spheroid shape in the shape of a football.

In another embodiment of the disclosure, an infusion system includes a pump, at least one sensor, a fluid delivery line connected to the pump for delivery fluid, a processor in electronic communication with the pump and the at least one sensor, and a memory in electronic communication with the processor. The memory includes programming code for execution by the processor. The programming code is configured to determine whether there is more than a threshold level of air in the fluid delivery line based on measurements taken by the at least one sensor. The fluid delivery line includes an inner passage extending longitudinally within the fluid delivery line. The inner passage includes an upstream portion, a downstream portion, and an orifice connecting the upstream portion to the downstream portion. The infusion system further includes: (1) the at least one sensor being disposed at the upstream portion, the orifice including an orifice inner diameter of 0.508 millimeters (0.020 inches) or smaller, and the upstream portion including a first volume which is at least 25 percent smaller than a second volume of fluid delivered by a stroke of the pump; (2) the at least one sensor being disposed at the upstream portion, the orifice including the orifice inner diameter of 0.508 millimeters (0.020 inches) or smaller, and an upstream portion inner diameter of the upstream portion being 2.286 millimeters (0.090 inches) or larger; (3) the at least one sensor being disposed at the downstream portion, and the downstream portion including a downstream portion inner diameter of 0.508 millimeters (0.020 inches) or smaller; or (4) the at least one sensor being disposed at the upstream portion, and a cross-section of the upstream portion including an elliptical shape or a prolate spheroid shape in the shape of a football.

In still another embodiment of the disclosure, a method is disclosed for operating an infusion system. In one step, a pump pumps fluid through a fluid delivery line. In another step, signals are emitted and received from at least one sensor into and from the fluid delivery line. In another step, measurements of the signals are processed, using a processor, to determine whether there is more than a threshold level of air in the fluid delivery line. In yet another step, an alarm is turned on when the processor determines that there is more than the threshold level of the air in the fluid delivery line. The fluid delivery line includes an inner passage extending longitudinally within the fluid delivery line. The inner passage includes an upstream portion, a downstream portion, and an orifice connecting the upstream portion to the downstream portion. The infusion system includes: (1) the at least one sensor being disposed at the upstream portion, the orifice including an orifice inner diameter of 0.508 millimeters (0.020 inches) or smaller, and the upstream portion including a first volume which is at least 25 percent smaller than a second volume of fluid delivered by a stroke of the pump; (2) the at least one sensor being disposed at the upstream portion, the orifice including an orifice inner diameter of 0.508 millimeters (0.020 inches) or smaller, and an upstream portion inner diameter of the upstream portion being 2.286 millimeters (0.090 inches) or larger; (3) the at least one sensor being disposed at the downstream portion, and the downstream portion including a downstream portion inner diameter of 0.508 millimeters (0.020 inches) or smaller; or (4) the at least one sensor being disposed at the upstream portion, and a cross-section of the upstream portion including an elliptical shape or a prolate spheroid shape in the shape of a football.

These and other features, aspects and advantages of the disclosure will become better understood with reference to the following drawings, description and claims.

BRIEF DESCRIPTION OF THE DRAWINGS

FIG. 4 illustrates a cross-section view through one embodiment of a segment of fluid delivery line with a stationary fluid droplet in the fluid delivery line between a transmitter portion of an air-in-line sensor and a receiver portion of the air-in-line sensor;

FIG. 5 illustrates a cross-section view through one embodiment of a segment of fluid delivery line with bouncing air bubbles remaining in the fluid delivery line between a transmitter portion of an air-in-line sensor and a receiver portion of an air-in-line sensor;

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims. It is noted that the Figures are purely for illustrative purposes and are not to scale.

Figure 1:
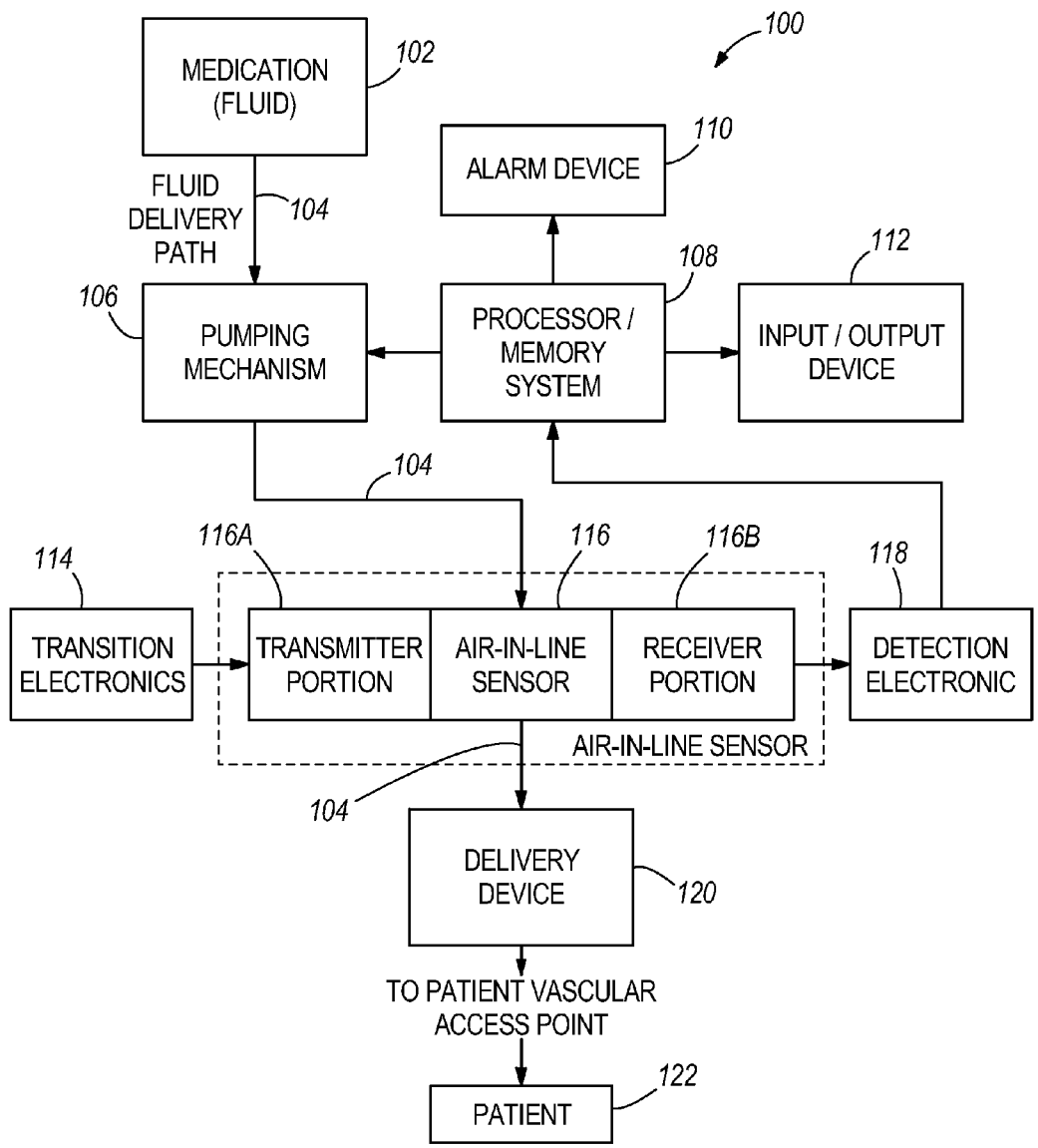
FIG. 1 illustrates a block diagram of a drug delivery infusion system under one embodiment of the disclosure.

FIG. 1 illustrates a block diagram of a drug delivery infusion system 100 under one embodiment of the disclosure. The drug delivery infusion system 100 comprises: a fluid supply container 102; a fluid delivery line 104; a pumping device 106; a processing device 108; an alarm device 110; an input/output device 112; an electronic transmitting device 114; an air-in-line sensor 116; an electronic detection device 118; and a delivery device 120. The drug delivery infusion system 100 may comprise a drug delivery infusion system such as the Plum A+™, Gemstar™, Symbig™, or other type of drug delivery infusion system. The fluid supply container 102 comprises a container for delivering fluid such as IV fluid, drug, or nutrition to the patient 122. The fluid delivery line 104 comprises one or more tubes, connected between the fluid supply container 102, the pumping device 106, the air-in-line sensor 116, and the delivery device 120, for transporting fluid from the fluid supply container 102, through the pumping device 106, through the air-in-line sensor 116, through the delivery device 120 to the patient 122. The pumping device 106 comprises a pump for pumping fluid from the supply container 102.

The pumping device 106 may comprise a plunger based pump, a peristaltic pump, or another type of pump. The processing device 108 includes a memory and a clock. The processing device 108 comprises a processor in electronic communication with the pumping device 106 and the electronic detection device 118 for processing information received from the air-in-line sensor 116 and for executing a software algorithm/programming code stored in the memory in electronic communication with the processing device 108 to determine if air, fluid, or a struck-fluid droplet is located in the fluid delivery line 104 at the location of the air-in-line sensor 116. For instance, the software algorithm/programming code is configured to determine whether there is more than a threshold level of air in the fluid delivery line 104. The alarm device 110 comprises an alarm, electronically coupled to and triggered by the processing device 108, for notifying the clinician as to the presence of excessive air (for instance when the programming code determines that there is more than the threshold level of air in the fluid delivery tube 104) or a stuck-fluid droplet in the fluid delivery line 104 at the location of the air-in-line sensor 116, and for stopping the pumping device 106 prior to an air embolism being delivered through the fluid delivery line 104 and the delivery device 120 to the patient 122. The input/output device 112 comprises a device which allows a clinician to input information, such as a user-inputted medication infusion program, to the processing device 108, and which also outputs information to the clinician.

The electronic transmitting device 114 comprises electronic circuitry, connected to the air-in-line sensor 116, which transmits a signal from a transmitter portion 116A of the air-in-line sensor 116, through fluid delivery line 104, to a receiver portion 116B of the air-in-line sensor 116 connected to the electronic detection device 118. The air-in-line sensor 116 is connected to the fluid delivery line 104 distal of the pumping device 106. In other embodiments, the air-in-line sensor 116 may be located proximal to the pumping device 106 or may be located in both proximal and distal positions. The transmitter and receiver portions 116A and 116B of the air-in-line sensor 116 sense the presence of air or fluid within the fluid delivery line 104. The transmitter and receiver portions 116A and 116B of the air-in-line sensor 116 comprise a transducer such as an ultrasonic sensor, an acoustic sensor, an optical sensor, or another type of sensor. The electronic detection device 118 comprises electronic circuitry, connected to the receiver portion 116B of the air-in-line sensor 116, for receiving the signal transmitted/emitted from the electronic transmitting device 114, through the transmitter portion 116A of the air-in-line sensor 116, through the fluid delivery line 104, to the receiver portion 116B of the air-in-line sensor 116, to the electronic detection device 118. Alternate arrangements of the sensor transmitter and receiver are possible and include both side-by-side arrangements and the use of a single transducer to both transmit and receive a reflected signal. The delivery device 120 comprises a patient vascular access point device for delivering fluid from the fluid supply container 102 to the patient 122. The delivery device 120 may comprise a needle, a catheter, or another type of delivery device.

Figure 2:
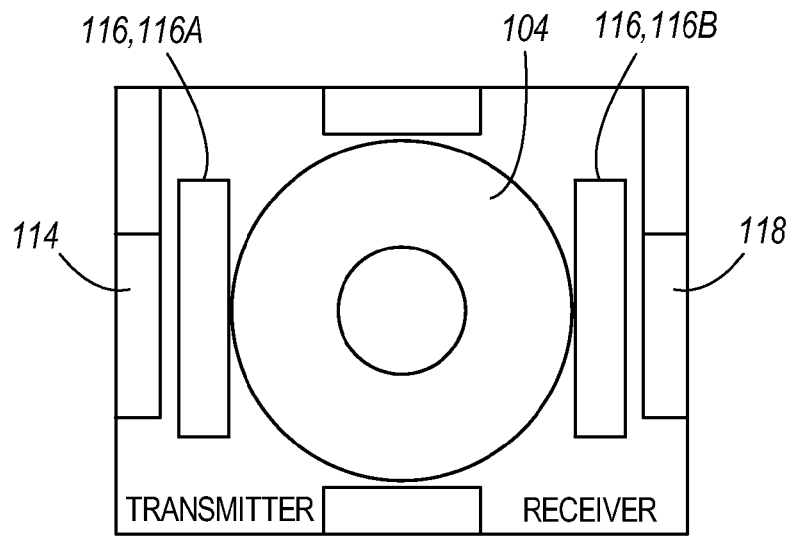
FIG. 2 illustrates a cross-section through one embodiment of a segment of fluid delivery line coupled to an electronic transmitting device, a transmitter portion of an air-in-line sensor, a receiver portion of an air-in-line sensor, and an electronic detection device.

FIG. 2 illustrates a cross-section through one embodiment of a segment of fluid delivery line 104 coupled to the electronic transmitting device 114, the transmitter portion 116A of the air-in-line sensor 116, the receiver portion 116B of the air-in-line sensor 116, and the electronic detection device 118. The transmitter and receiver portions 116A and 116B of the air-in-line sensor 116 comprises piezoelectric crystals compressed against each side of the fluid delivery line 104 creating more surface area for uniform acoustic coupling and better signal to noise ratio. This arrangement of the transmitter and receiver portions 116A and 116B of the air-in-line sensor 116 enables the transmission and detection of an ultrasonic signal through a target volume of the infusion line fluid delivery line 104. The electronic transmitting device 114 generates a nominal 5.25 MHz ultrasonic signal directed from the transmitter 116A portion of the air-in-line sensor 116, through the fluid delivery line 104, to the receiver portion 116B of the air-in-line sensor 116 connected to the electronic detection device 118. When fluid is present in the fluid delivery line 104 at the position of the air-in-line sensor 116, the receiver portion 116B of the air-in-line sensor 116 and the electronic detection device 118 receives a larger electrical signal than when air is present at the same position. Because of an inversion in the electronics of the electronic detection device 118, the software of the processing device 108 will receive a low signal when fluid is present at the location of the air-in-line sensor 116, and a high signal when air is present at the location of the air-in-line sensor 116. When a cassette is loaded into the pumping device 106, the segment of the fluid delivery line 104 distal to the cassette is clamped into place in front of the air-in-line sensor 116. This enables reliable and repeatable sensor performance over multiple cassettes.

Figure 3:
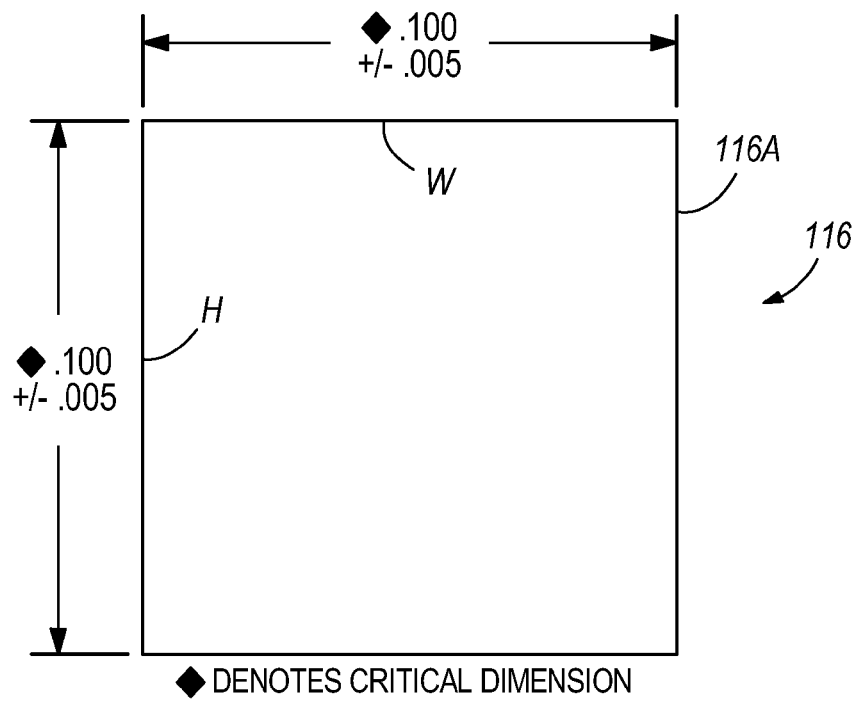
FIG. 3 illustrates a top view through one embodiment of piezoelectric crystals of a transmitter portion of an air-in-line sensor.

FIG. 3 illustrates a top view through one embodiment of the piezoelectric crystals of the transmitter portion 116A of the air-in-line sensor 116. As shown, the height H of the air-in-line sensor 116 comprises 2.54 millimeters (0.100 inches) and the width W of the air-in-line sensor 116 comprise 2.54 millimeters (0.100 inches). The dimensions of the receiver portion 116B of the air-in-line sensor 116 are identical to the transmitter portion 116A of the air-in-line sensor 116. In other embodiments, the dimensions of the transmitter and receiver portions 116A and 116B of the air-in-line sensor 116 may vary.

Viewing FIG. 2, the ability of the ultrasonic signal to propagate from the transmitter portion 116A to the receiver portion 116B of the air-in-line sensor 116 is governed by the acoustic impedance of the materials. The matching layers of the transducers of the transmitter and receiver portions 116A and 116B are designed to control the amplitude of the reflections at the piezo-matching layer and matching layer-fluid delivery line interfaces. The other significant component of the signal path is the fluid or air inside the fluid delivery line 104. The acoustic impedances (Za) @ 20° C. of interest are as follows: water=$1.5 \times 10^6$ kg/(m$^2$s); PVC=$3.3 \times 10^6$ kg/(m$^2$s); and air=413.2 kg/(m$^2$s). Reflections of the ultrasonic signal occur at material boundaries and are governed by the differences in acoustic impedance. The reflection coefficient (RC) is defined as: RC=(Za−Za1)/(Za+Za1). A high RC indicates that the signal will not pass through the boundary. For the PVC to water interface, the RC=0.375 which indicates that a majority of the signal will pass through the interface. For the PVC to air interface, the RC=0.999 which indicates that none of the signal will pass through the interface, thus indicating most of the signal must pass through the fluid delivery line 104.

The electronic detection device 118 converts the signal received by the receiver portion 116B of the air-in-line sensor 116 back to an electrical signal as governed by the equation: Vout=$\lambda$ Tpiezo $\sigma$/Drvr, where Vout=the electrical signal received by the receiver portion 116B of the air-in-line sensor; $\lambda$=the strain on the piezo crystal due to the ultrasonic wave; $\sigma$=the stress on the piezo crystal due to the ultrasonic wave; Tpiezo=the thickness of the piezo crystal; Drvr=the mechanical displacement of the piezo by the ultrasonic crystal. Thus, when fluid is in the fluid delivery line 104, the receiver portion 116B of the air-in-line sensor 116 is able to collect a large amount of ultrasonic energy since fluid is a better conductor then air. This appears as a low voltage at the A/D converter of the electronic detection device 118 because the signal received by the receiver portion 116B of the air-in-line sensor 116 is inverted electrically. The position of the droplet inside the fluid delivery line 104 relative to the transmitter and receiver portions 116A and 116B of the air-in-line sensor 116 also influences the amount of energy the receiver portion 116B of the air-in-line sensor detects. When air is in the fluid delivery line 104, the receiver portion 116B of the air-in-line sensor 116 receives little energy, or a smaller fraction of the energy from the original transmitted energy.

FIG. 4 illustrates a cross-section view through one embodiment of a segment of fluid delivery line 104 with a stationary fluid droplet 124 in the fluid delivery line 104 between the transmitter portion 116A of the air-in-line sensor 116 and the receiver portion 116B of the air-in-line sensor 116. The stationary fluid droplet 124 has separated from the trailing surface 125 of fluid 127 that was being pumped through the fluid delivery line 104 by the pumping device 106 (shown in FIG. 1). The trailing surface 125 occurred because the fluid supply container 102 (shown in FIG. 1) emptied during the infusion, producing an end-of-bag event, leaving only air 129 to be pumped through the fluid delivery line 104. The fluid droplet 124 may remain stuck in this location if the forces exerted by gravity and the flow of pumped air 129 cannot overcome the liquid surface tension forces that keeps the fluid droplet 124 in place. When a fluid droplet 124 is stationary in the fluid delivery line 104 by the air-in-line sensor 116, the fluid droplet 124 provides a better path than air 129 alone and the receiver portion 116B of the air-in-line sensor 116 collects more energy than if just air 129 was present at the air-in-line sensor 116. The formation of a stuck (or stationary) droplet 124 occurs all along the fluid delivery line segment 104 when there is a transition from fluid delivery to air delivery. If the stuck droplet 124 forms between the transmitter and receiver portions 116A and 116B of the air-in-line sensor 116, as shown in FIG. 4, an acoustic short circuit results leading to a decrease in the digitized air sensor voltage (analog-to-digital counts or "ADC") received and inverted by the electronic detection device 118 of FIGS. 1 and 2. It is noted that even if the stuck droplet 124 only partially fills (as opposed to completely filling) the fluid delivery line 104 at the air-in-line sensor 116, the acoustic short circuit can still result. If the energy collected by receiver portion 116B as a result of the stuck droplet 124 was more than the air/fluid threshold programmed in the software of most current air-detection systems, most current air detection systems would indicate that they had detected fluid when in fact air was present in the fluid delivery line 104 at the air-in-line sensor 116. As a result, in most current air detection systems, when an end-of-bag event occurs the stuck droplet 124 tricks the system into believing that fluid, rather than air, is being pumped through the fluid delivery line 104 and as a result the alarm device 110 (shown in FIG. 1) is not triggered which would have indicated that air was in the fluid delivery line 104.

FIG. 5 illustrates a cross-section view through one embodiment of a segment of fluid delivery line 104 with bouncing air bubbles 126 remaining in the fluid delivery line 104 between the transmitter portion 116A of the air-in-line sensor 116 and the receiver portion 116B of the air-in-line sensor 116. In this situation, the bouncing air bubbles 126 oscillate vertically near the air-in-line sensors 116 rather than traveling distally with the fluid 127 being pumped by the pumping device 106 (shown in FIG. 1) through the fluid delivery line 104. In this case, the same population of bouncing air bubbles 126 will be sensed repeatedly over a prolonged period of time, and the associated air volume will be calculated and accumulated by the air-in-line algorithm being run by the processing device 108 (shown in FIG. 1) until the alarm device 110 (shown in FIG. 1) is triggered. This event is considered to be a nuisance alarm because the calculated air volume is artificially elevated and is not actually being delivered toward the patient. If the bouncing air bubbles are not purged from the sensing zone, then the alarm device 110 will trigger again and again, each time requiring intervention by the clinician. The bouncing air bubbles 126 in the fluid delivery line 104 are caused by the pumping device 106 (shown in FIG. 1) generating a series of flow pulses transporting the fluid 127 and bouncing air bubbles 126 downward distally through the fluid delivery line 104 with, due to gravity driven buoyancy, the bouncing air bubbles 126 traveling back upward within the fluid delivery line 104 in-between pulses to remain located at the air-in-line sensors 116.

Unique configurations (i.e. geometries) for the fluid delivery line 104 of the drug delivery infusion system 100 of FIG. 1 have been discovered to improve the detection of air in the fluid delivery line 104 and end-of-bag events (i.e. an empty fluid supply container 102) during an infusion of fluid into a patient without having to exclusively rely on complex algorithms. These unique configurations for the fluid delivery line 104 reduce the unwanted interference of oscillating air bubbles in the air sensing zone at the air-in-line sensors 116 during an infusion of fluid into a patient thereby reducing the occurrence of air-in-line nuisance alarms which are false-positives measurements of total air volume within the fluid delivery line 104 falsely indicating that the total air within the fluid delivery line 104 has exceeded a total air threshold. These unique configurations for the fluid delivery line 104 further reduce the unwanted interference of stuck fluid droplets that remain stuck in the fluid delivery line 104 in the air sensing zone at the air-in-line sensor 116 after the fluid in the fluid supply container 102 has been consumed (i.e. an end-of-bag event). This is important as a struck fluid droplet can prevent the air-in-line sensor 116 from identifying an emptied fluid supply container 102, thereby allowing the pumping device 116 to continue pumping air towards the patient without the alarm device 110 turning on to indicate the presence of air in the fluid delivery line 104. These unique configurations of the fluid delivery line 104 may be used alone or in conjunction with algorithms, tailored to these unique configurations of the fluid delivery line 104, to improve the detection of air-in-line and end-of-bag events in the fluid delivery line 104.

Figure 6:
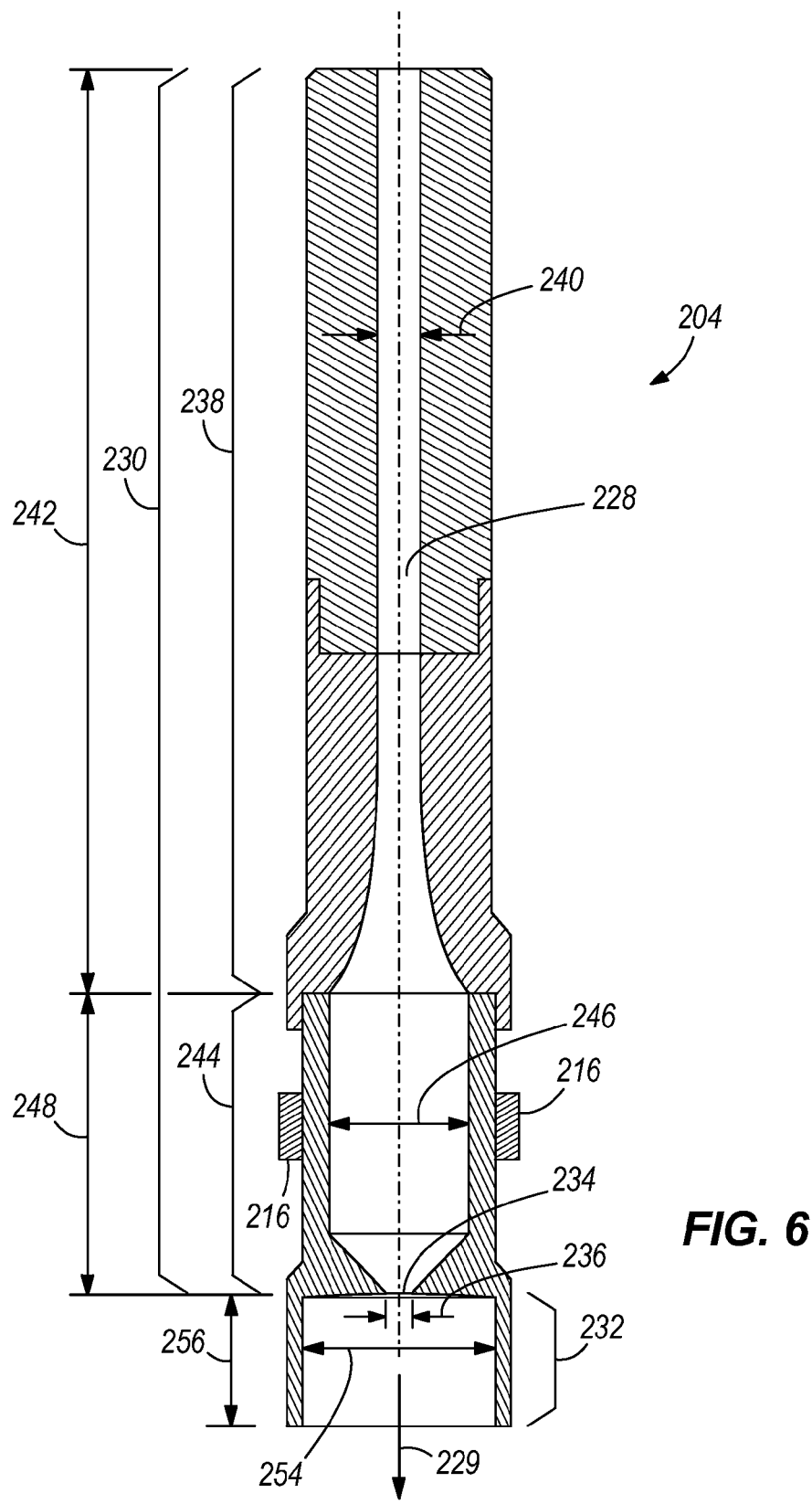
FIG. 6 illustrates a cross-section view through one embodiment of a first unique configuration of a fluid delivery line which may improve the detection of air in the fluid delivery line and end-of-bag events during an infusion of fluid into a patient.

FIG. 6 illustrates a cross-section view through one embodiment of a first unique configuration of a fluid delivery line 204 which may be substituted for the fluid delivery line 104 of the drug delivery infusion system 100 of FIG. 1 in order to improve the detection of air in the fluid delivery line 204 and end-of-bag events (i.e. an empty fluid supply container 102 shown in FIG. 1) during an infusion of fluid into a patient without having to exclusively rely on complex algorithms. The fluid delivery line 204 comprises an inner passage 228 extending longitudinally within the fluid delivery line 204 with fluid pumped through the inner passage 228 by the pumping device 106 (shown in FIG. 1) in flow-direction 229. The inner passage 228 comprises an upstream portion 230, a downstream portion 232, and an orifice 234 connecting the upstream portion 230 to the downstream portion 232. The orifice 234 comprises an orifice inner diameter 236 of 0.508 millimeters (0.020 inches) or smaller. The upstream portion 230 comprises a first upstream portion 238 having a first upstream portion inner diameter 240 of 0.762 millimeters (0.030 inches) or smaller and a first upstream portion length 242 in a range of 12.7 millimeters (0.500 inches) to 19.05 millimeters (0.750 inches), and a second upstream portion 244, in-between the first upstream portion 238 and the orifice 234, having a second upstream portion inner diameter 246 of 2.286 millimeters (0.090 inches) or larger and a second upstream portion length 248 in a range of 3.81 millimeters (0.150 inches) to 6.35 millimeters (0.250 inches). The upstream portion 230 comprises a first volume which is at least 25 percent smaller than a second volume of fluid delivered by a stroke of the pumping device 106 (shown in FIG. 1). The downstream portion 232 comprises a downstream portion inner diameter 254 in a range of 1.3716 millimeters (0.054 inches) to 2.54 millimeters (0.100 inches) and a downstream portion length 256 in a range of 6.35 millimeters (0.250 inches) to 12.7 millimeters (0.500 inches). The air-in-line sensors 216 (which are identical to the air-in-line sensors 116 of FIG. 1) are disposed at the second upstream portion 244.

The configuration of FIG. 6 reduces bouncing air bubbles at the air-in-line sensors 216 due to the orifice 234 having the orifice inner diameter 236 of 0.508 millimeters (0.020 inches) or smaller which is sufficiently small to prevent buoyancy forces from transporting air back through the orifice 234 to the air-in-line sensors 216, particularly during the time periods when the fluid in the fluid delivery line 204 is relatively still. Additionally, all air is forced to be pumped through the orifice 234 past the air-in-line sensors 216 due to the upstream portion 230 comprising the first volume which is at least 25 percent smaller than the second volume of the fluid delivered by each stroke of the pumping device 106 (shown in FIG. 1). These features reduce air-in-line nuisance alarms of the airin-line alarm device 110 (shown in FIG. 1) by allowing the air-in-line sensors 216 to measure the volume of pumped air only once, and not multiple times.

The configuration of FIG. 6 reduces the issues associated with stuck fluid droplets at the air-in-line sensors 216 due to the upstream portion 230 comprising the second upstream portion inner diameter 246 of 2.286 millimeters (0.090 inches) or larger at the air-in-line sensors 216. As a result of the large relative size of the second upstream portion inner diameter 246 of the upstream portion 230, any residual fluid droplet in the upstream portion 230 at the air-in-line sensors 216 will tend to be much smaller in size compared to the large relative size of the second upstream portion inner diameter 246 of the upstream portion 230. As a result, the fluid droplet will be incapable of transmitting a large amount of acoustic energy across the cross-section of the upstream portion 230 at the air-in-line sensors 216 (relative to when the cross-section of the upstream portion 230 is fully occupied by fluid), and the air-in-line sensors 216 will be able to detect the air and trigger the air-in-line alarm device 110 (shown in FIG. 1) before the air is pumped to the patient.

Figure 7:
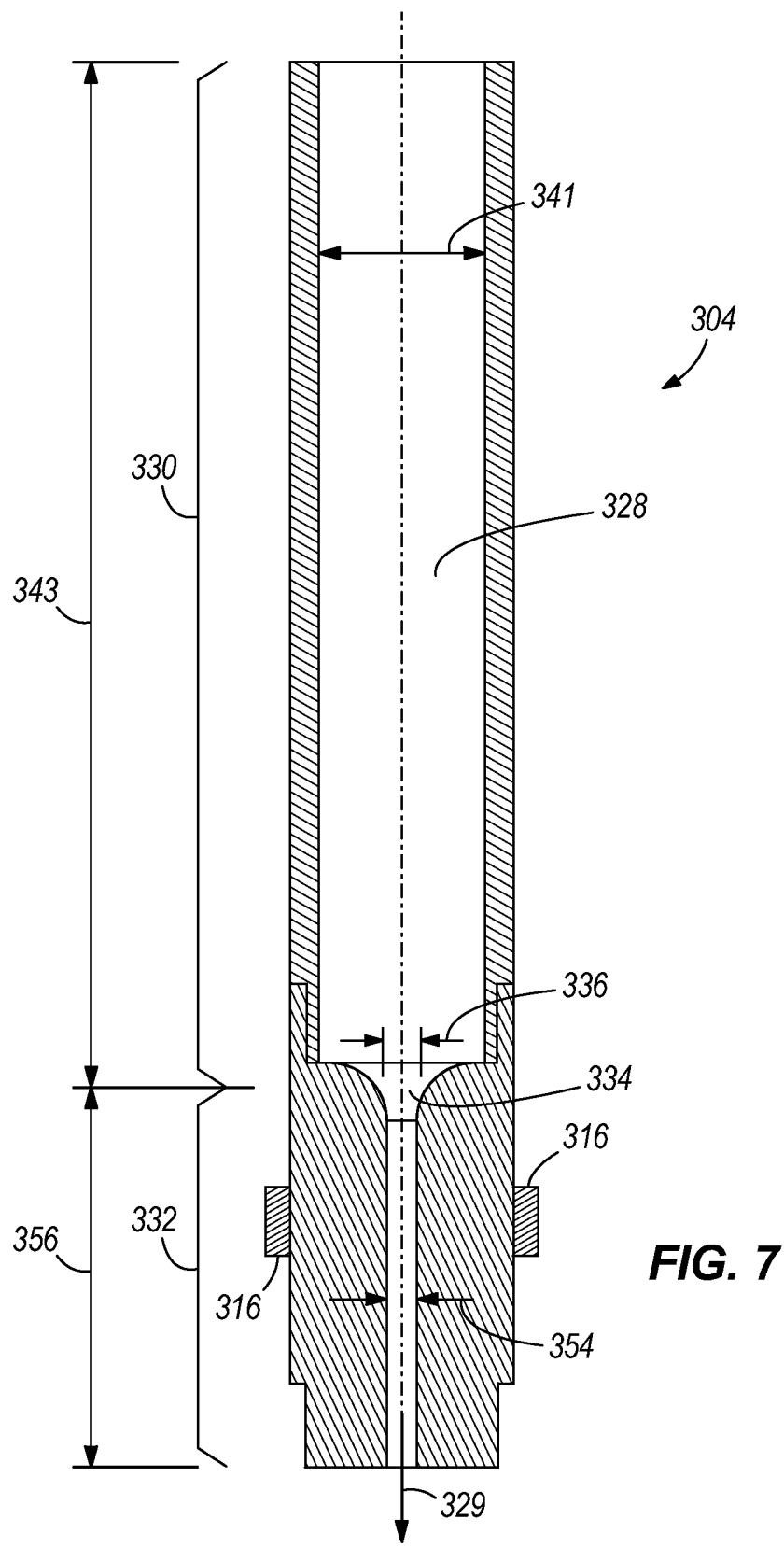
FIG. 7 illustrates a cross-section view through another embodiment of a second unique configuration of a fluid delivery line which may improve the detection of air in the fluid delivery line and end-of-bag events during an infusion of fluid into a patient

FIG. 7 illustrates a cross-section view through another embodiment of a second unique configuration of a fluid delivery line 304 which may be substituted for the fluid delivery line 104 of the drug delivery infusion system 100 of FIG. 1 in order to improve the detection of air in the fluid delivery line 304 and end-of-bag events (i.e. an empty fluid supply container 102 shown in FIG. 1) during an infusion of fluid into a patient without having to exclusively rely on complex algorithms. The fluid delivery line 304 comprises an inner passage 328 extending longitudinally within the fluid delivery line 304 with fluid pumped through the inner passage 328 by the pumping device 106 (shown in FIG. 1) in flow-direction 329. The inner passage 328 comprises an upstream portion 330, a downstream portion 332, and an orifice 334 connecting the upstream portion 330 to the downstream portion 332. The orifice 334 comprises an orifice inner diameter 336 of 0.508 millimeters (0.020 inches) or smaller. The upstream portion 330 comprises an upstream portion inner diameter 341 of 2.286 millimeters (0.090 inches) or larger and an upstream portion length 343 in a range of 12.7 millimeters (0.500 inches) to 19.05 millimeters (0.750 inches). The upstream portion 330 comprises a first volume which is at least 25 percent smaller than a second volume of the fluid delivered by a stroke of the pumping device 106 (shown in FIG. 1). The downstream portion 332 comprises a downstream portion inner diameter 354 of 0.508 millimeters (0.020 inches) or smaller and a downstream portion length 356 of 6.35 millimeters (0.250 inches) or longer. The air-in-line sensors 316 (which are identical to the air-in-line sensors 116 of FIG. 1) are disposed at the downstream portion 332.

The configuration of FIG. 7 reduces bouncing air bubbles at the air-in-line sensors 316 due to the downstream portion 332 comprising the downstream portion inner diameter 354 of 0.508 millimeters (0.020 inches) or smaller and the downstream portion length 356 of 6.35 millimeters (0.250 inches) or longer, with these dimensions being sufficiently small to prevent buoyancy forces from transporting air back through the downstream portion 332 back to the air-in-line sensors 316 (after the air has already traveled past the air-in-line sensors 316), particularly during the time periods when the fluid in the fluid delivery line 304 is relatively still. Additionally, all air is forced to be pumped through the orifice 334 past the air-in-line sensors 316 due to the upstream portion 330 comprising the first volume which is at least 25 percent smaller than the second volume of the fluid delivered by each stroke of the pumping device 106 (shown in FIG. 1). These features reduce air-in-line nuisance alarms of the air-in-line alarm device 110 (shown in FIG. 1) by allowing the air-in-line sensors 316 to measure the volume of pumped air only once, and not multiple times.

The configuration of FIG. 7 reduces the issues associated with stuck fluid droplets at the air-in-line sensors 316 due to the downstream portion 332 comprising the downstream portion inner diameter 354 of 0.508 millimeters (0.020 inches) or smaller because a fluid droplet will tend to span substantially across the cross-section of the downstream portion 332 via surface tension forces thus allowing the pumped air to force the fluid droplet past the air-in-line sensors 316 and out of the downstream portion 332. Any fluid droplets which are too small to span the cross-section of the downstream portion 332 and be forced out by the air will likely be too small to transmit a large amount of acoustic energy across the downstream portion 332 at the air-in-line sensors 316 (relative to when the cross-section of the downstream portion 332 is fully occupied by fluid), thus allowing the air-in-line sensors 316 to detect the air and trigger the air-in-line alarm device 110 (shown in FIG. 1) before the air is pumped to the patient.

Figure 8:
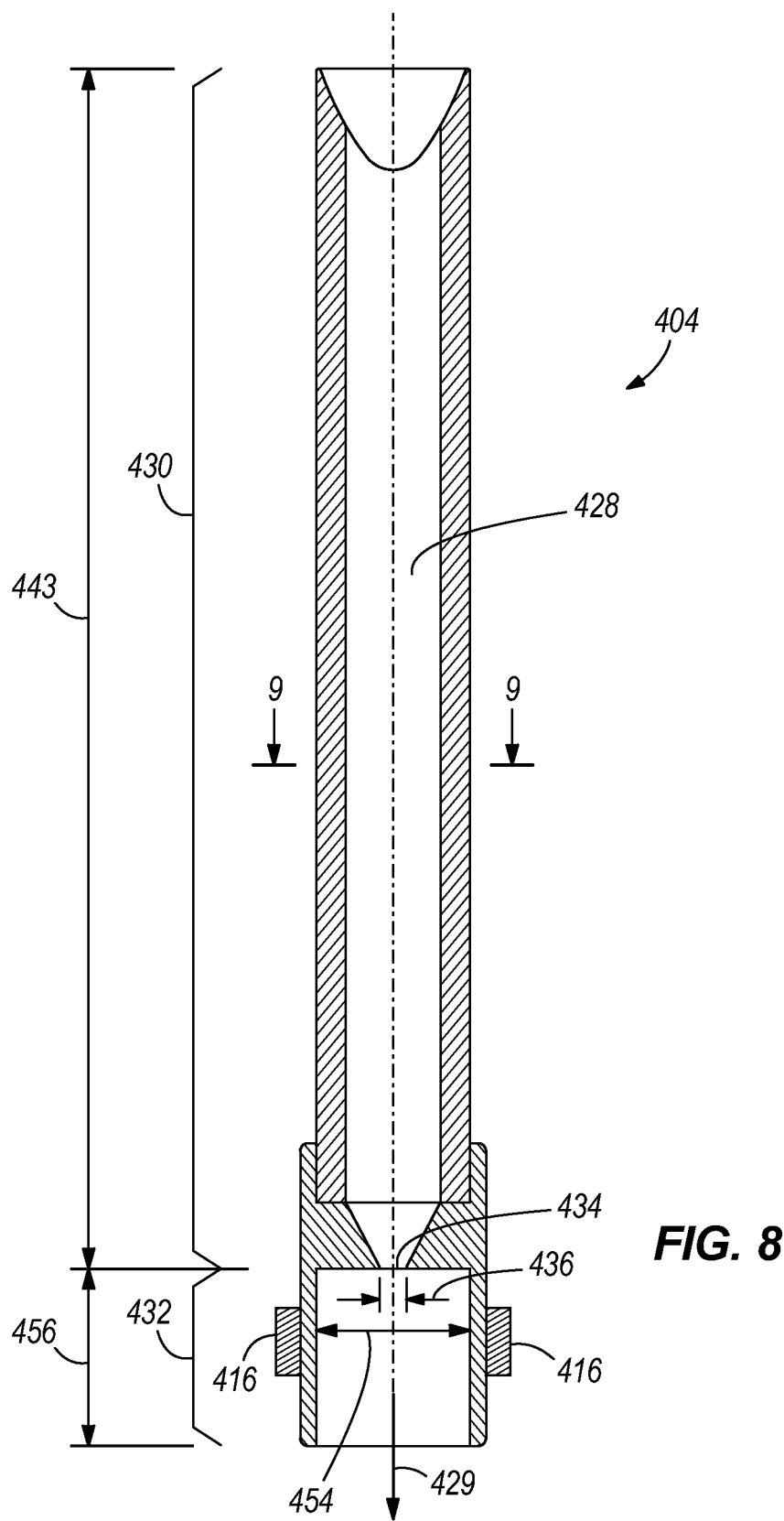
FIG. 8 illustrates a cross-section view through another embodiment of a third unique configuration of a fluid delivery line which may improve the detection of air in the fluid delivery line and end-of-bag events during an infusion of fluid into a patient.

FIG. 8 illustrates a cross-section view through another embodiment of a third unique configuration of a fluid delivery line 404 which may be substituted for the fluid delivery line 104 of the drug delivery infusion system 100 of FIG. 1 in order to improve the detection of air in the fluid delivery line 404 and end-of-bag events (i.e. an empty fluid supply container 102 shown in FIG. 1) during an infusion of fluid into a patient without having to exclusively rely on complex algorithms. The fluid delivery line 404 comprises an inner passage 428 extending longitudinally within the fluid delivery line 404 with fluid pumped through the inner passage 428 by the pumping device 106 (shown in FIG. 1) in flow-direction 429. The inner passage 428 comprises an upstream portion 430, a downstream portion 432, and an orifice 434 connecting the upstream portion 430 to the downstream portion 432. The orifice 434 comprises an orifice inner diameter 436 of 0.508 millimeters (0.020 inches) or smaller. The upstream portion 430 comprises a first volume which is at least 25 percent smaller than a second volume of the fluid delivered by a stroke of the pumping device 106 (shown in FIG. 1). The downstream portion 432 comprises a downstream portion inner diameter 454 ranging between 1.3716 millimeters (0.054 inches) to 2.54 millimeters (0.100 inches) and a downstream portion length 456 ranging between 6.35 millimeters (0.250 inches) to 12.7 millimeters (0.500 inches).

Figure 9:
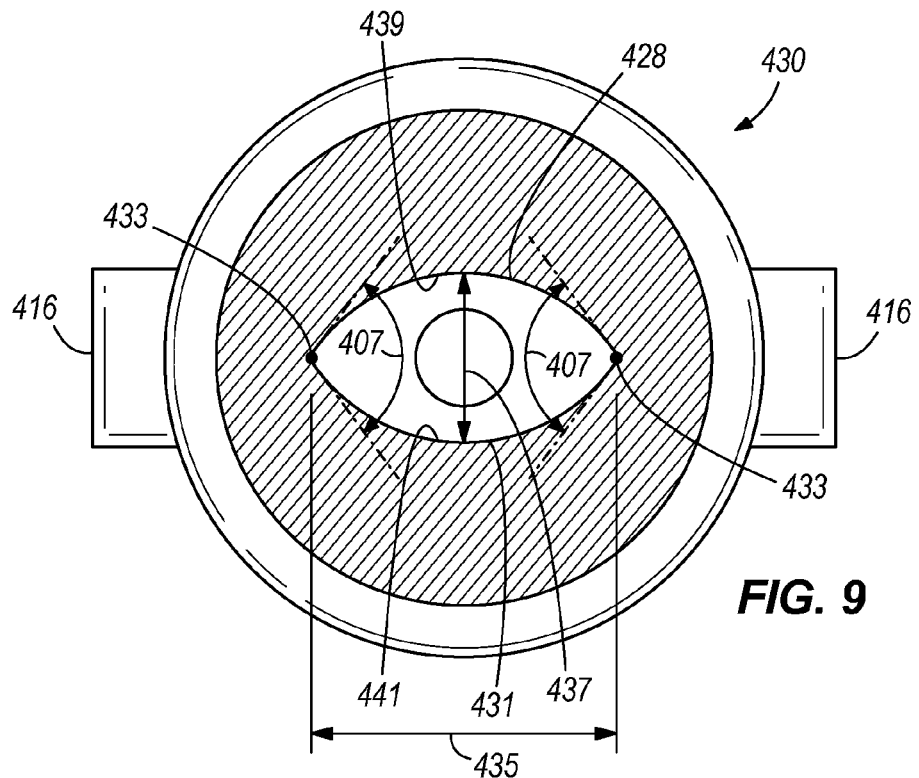
FIG. 9 illustrates a cross-section view through line 9-9 of the embodiment of FIG. 8.

FIG. 9 illustrates a cross-section view through line 9-9 of the upstream portion 430 of the embodiment of FIG. 8. As shown in FIG. 9, the cross-section view of the upstream portion 430 comprises a prolate spheroid shape 431 in the shape of a football. Air-in-line sensors 416 (which are identical to the air-in-line sensors 116 of FIG. 1) are disposed at opposed corners 433 of the prolate spheroid shape in the shape of the football. The opposed corners 433 comprise angles 407 of the inner passage 428 ranging between 15 degrees to 45 degrees. The distance 435 between the opposed corners 433 may range between 1.27 millimeters (0.050 inches) to 2.54 millimeters (0.100 inches). The distance 437 between the opposed surfaces 439 and 441 may range between 0.508 millimeters (0.020 inches) to 2.032 millimeters (0.080 inches). The length 443 of the upstream portion 430 of FIG. 8 may range between 12.7 millimeters (0.500 inches) to 19.05 millimeters (0.750 inches).

Figure 10:
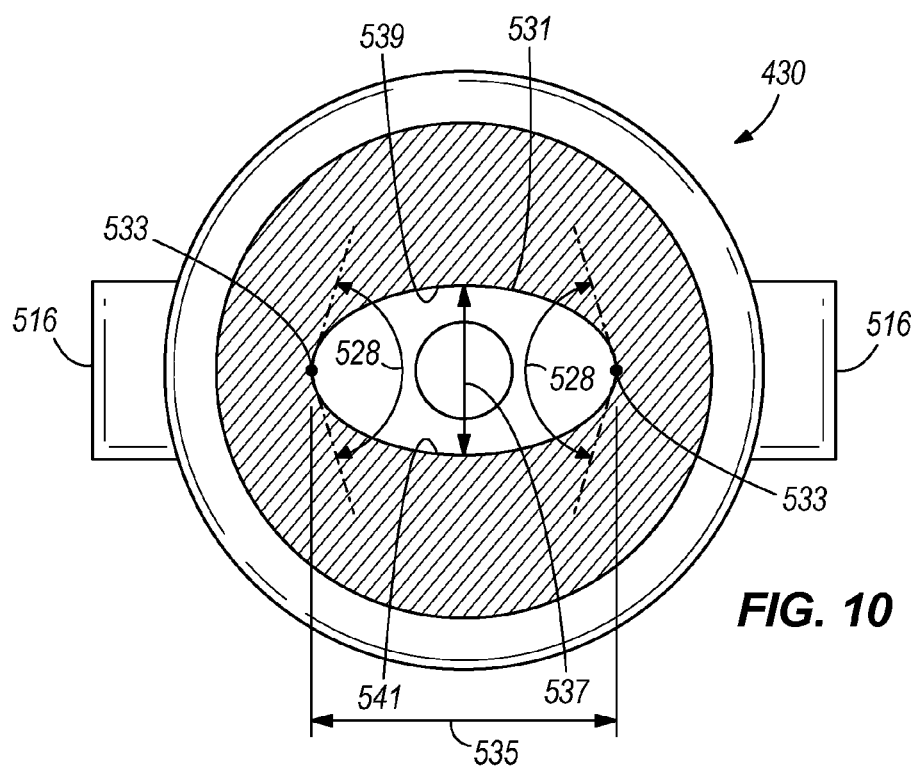
FIG. 10 illustrates an alternative cross-section view through line 9-9 of the embodiment of FIG. 8.

FIG. 10 illustrates an alternative cross-section view through line 9-9 of the upstream portion 430 of the embodiment of FIG. 8. As shown in FIG. 10, the alternative cross-section view of the upstream portion 430 may comprise an elliptical shape 531. Air-in-line sensors 516 (which are identical to the air-in-line sensors 116 of FIG. 1) are disposed at opposed corners 533 of the elliptical shape. The opposed corners 533 comprise angles of the inner passage 528 ranging between 15 degrees to 45 degrees. The distance 535 between the opposed corners 533 may range between 1.27 millimeters (0.050 inches) to 2.54 millimeters (0.100 inches). The distance 537 between the opposed surfaces 539 and 541 may range between 0.508 millimeters (0.020 inches) to 2.032 millimeters (0.080 inches). In other embodiments, the cross-section through line 9-9 of the upstream portion 430 of the embodiment of FIG. 8 may comprise a variety of non-circular shapes having corners into which sensors may be placed.

The configuration of FIGS. 8-10 reduce bouncing air bubbles at the air-in-line sensors 416 (FIG. 9) and 516 (FIG. 10) due to the orifice 434 having the orifice inner diameter 436 of 0.508 millimeters (0.020 inches) or smaller which is sufficiently small to prevent buoyancy forces from transporting air back through the orifice 434 to the air-in-line sensors 416 (FIG. 9) and 516 (FIG. 10), particularly during the time periods when the fluid in the fluid delivery line 404 is relatively still. Additionally, all air is forced to be pumped through the orifice 434 past the air-in-line sensors 416 (FIG. 9) and 516 (FIG. 10) due to the upstream portion 430 comprising the first volume which is at least 25 percent smaller than the second volume of the fluid delivered by each stroke of the pumping device 106 (shown in FIG. 1). These features reduce air-in-line nuisance alarms of the air-in-line alarm device 110 (shown in FIG. 1) by allowing the air-in-line sensors 416 (FIG. 9) and 516 (FIG. 10) to measure the volume of pumped air only once, and not multiple times.

The configuration of FIGS. 8-10 reduce the issues associated with stuck fluid droplets at the air-in-line sensors 416 (FIG. 9) and 516 (FIG. 10) due to the opposed corners 433 (FIG. 9) and 533 (FIG. 10) drawing a residual fluid droplet into one of these corners via surface tension (capillary) force so that the fluid droplet will not bridge the gap between the air-in-line sensors 416 (FIG. 9) and 516 (FIG. 10). The fluid droplet will therefore be incapable of transmitting acoustic energy across the distance 435 (FIG. 9) and 535 (FIG. 10) between the air-in-line sensors 416 (FIG. 9) and 516 (FIG. 10) allowing them to detect the remaining air and trigger the air-in-line alarm device 110 (shown in FIG. 1) before the air is pumped to the patient.

Testing of the unique configurations of FIGS. 6-10 has demonstrated that the particular sizes and shapes of these configurations substantially reduce the prevalence of bouncing air-bubbles and stuck fluid droplets at the air-in-line sensors over the configurations of current infusion systems. This results in more accurate air-in-line detection including reduced false air-in-line alarms due to bouncing air bubbles at the sensor, and reduced risk of the non-detection (a false negative) of air in the line due to the presence of a stuck fluid droplet at the sensor.

Figure 11:
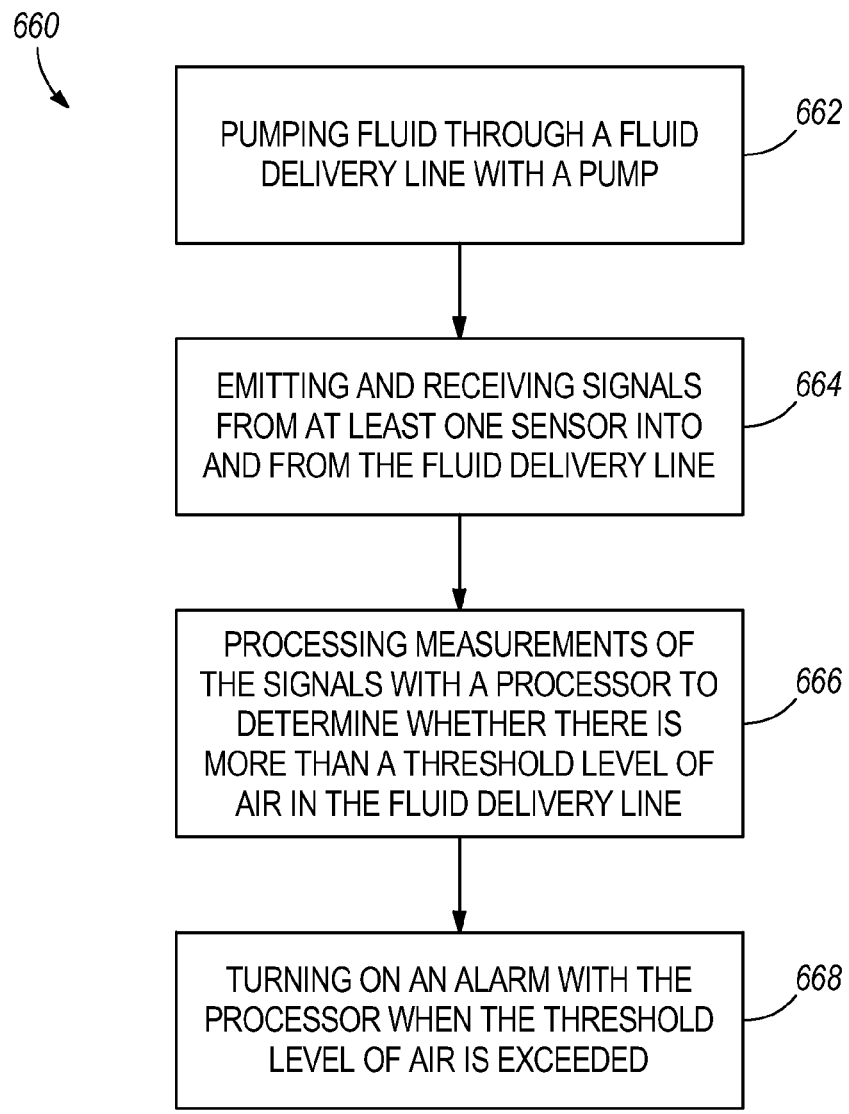
FIG. 11 is a flowchart illustrating one embodiment of a method for operating an infusion system

FIG. 11 is a flowchart illustrating one embodiment of a method 660 for operating an infusion system. In step 662, fluid is pumped with a pump through a fluid delivery line. In step 664, signals are emitted and received from at least one sensor into and from the fluid delivery line. In step 666, a processor processes measurements of the signals to determine whether there is more than a threshold level of air in the fluid delivery line. In step 668, the processor turns on an alarm when the processor determines that there is more than a threshold level of air in the fluid delivery line.

The fluid delivery line of the method 660 comprises an inner passage, extending longitudinally within the fluid delivery line, comprising: an upstream portion; a downstream portion; and an orifice connecting the upstream portion to the downstream portion. In one embodiment of the method 660, the inner passage may comprise the at least one sensor disposed at the upstream portion with the orifice comprising an orifice inner diameter of 0.508 millimeters (0.020 inches) or smaller, and the upstream portion comprising a first volume which is at least 25 percent smaller than a second volume of fluid delivered by a stroke of the pump. In another embodiment of the method 660, the inner passage may comprise the at least one sensor disposed at the upstream portion with the orifice comprising an orifice inner diameter of 0.508 millimeters (0.020 inches) or smaller, and an upstream portion inner diameter of the upstream portion being 2.286 millimeters (0.090 inches) or larger. In yet another embodiment of the method 660, the inner passage may comprise the at least one sensor disposed at the downstream portion having a downstream portion inner diameter of 0.508 millimeters (0.020 inches) or smaller. In still another embodiment of the method 660, the inner passage may comprise the at least one sensor disposed at the upstream portion with a cross-section of the upstream portion comprising an elliptical shape or a prolate spheroid shape in the shape of a football.

In an additional embodiment of the method 660, the at least one sensor may be disposed at the upstream portion with the orifice comprising the orifice inner diameter of 0.508 millimeters (0.020 inches) or smaller, the upstream portion comprising a first volume which is at least 25 percent smaller than a second volume of fluid delivered by the stroke of the pump, and the upstream portion inner diameter of the upstream portion being 2.286 millimeters (0.090 inches) or larger. In yet another embodiment of the method 660, the at least one sensor may be disposed as the downstream portion with the upstream portion comprising a first volume which is at least 25 percent smaller than a second volume of fluid delivered by a stroke of the pump, the downstream portion comprising a downstream portion inner diameter of 0.508 millimeters (0.020 inches) or smaller, and the downstream portion having a length of 6.35 millimeters (0.250 inches) or longer. In still another embodiment of the method 660, the cross-section of the upstream portion may comprise an elliptical shape or a prolate spheroid shape in the shape of a football, sensors may be disposed at opposed corners of the elliptical shape or the prolate spheroid shape, the opposed corners may comprise angles of the inner passage ranging between 15 to 45 degrees, and the upstream portion may comprise a first volume which is at least 25 percent smaller than a second volume of fluid delivered by the stroke of the pump. In other embodiments of the method 660, one or more of the steps may be not followed, may be modified in substance or in order, or one or more additional steps may be added.

One or more embodiments of the disclosure overcome one or more issues of the existing art by providing unique inner passage configurations to improve the in-line detection of air in a fluid delivery line of an infusion system by reducing the false-positive problems associated with the presence of bouncing air bubbles in the fluid delivery line and y reducing the false-negative problems associated with stuck fluid droplets in the fluid delivery line. These unique inner passage configurations may be used exclusively or may be used in conjunction with one or more algorithms to improve the in-line detection of air in a fluid delivery line of an infusion system by reducing the problems associated with the presence of bouncing air bubbles and stuck fluid droplets in the fluid delivery line since it is difficult to account for every situation through the use of algorithms alone.

It should be understood, of course, that the foregoing relates to exemplary embodiments of the disclosure and that modifications may be made without departing from the scope of the disclosure as set forth in the following claims.

We claim:

1. An infusion system comprising:
   at least one sensor;
   a fluid delivery line comprising an inner passage extending longitudinally within the fluid delivery line, wherein the inner passage comprises:
   an upstream portion;
   a downstream portion; and
   an orifice connecting the upstream portion to the downstream portion;
   wherein: (1) the infusion system further comprises a pump, the at least one sensor is disposed at the upstream portion, the orifice comprises an orifice inner diameter of 0.508 millimeters (0.020 inches) or smaller, and the upstream portion comprises a first volume which is at least 25 percent smaller than a second volume of fluid delivered by a stroke of the pump; (2) the at least one sensor is disposed at the upstream portion, the orifice comprises the orifice inner diameter of 0.508 millimeters (0.020 inches) or smaller, and an upstream portion inner diameter of the upstream portion is 2.286 millimeters (0.090 inches) or larger; (3) the at least one sensor is disposed at the downstream portion, and the downstream portion comprises a downstream portion inner diameter of 0.508 millimeters (0.020 inches) or smaller; or (4) the at least one sensor is disposed at the upstream portion, and a cross-section of the upstream portion comprises an elliptical shape or a prolate spheroid shape in the shape of a football.

2. The infusion system of claim 1 further comprising the pump, wherein the at least one sensor is disposed at the upstream portion, the orifice comprises the orifice inner diameter of 0.508 millimeters (0.020 inches) or smaller, and the upstream portion comprises the first volume which is at least 25 percent smaller than the second volume of the fluid delivered by the stroke of the pump.

3. The infusion system of claim 1 wherein the at least one sensor is disposed at the at the upstream portion, the orifice comprises the orifice inner diameter of 0.508 millimeters (0.020 inches) or smaller, and the upstream portion inner diameter of the upstream portion is 2.286 millimeters (0.090 inches) or larger.

4. The infusion system of claim 3 wherein the upstream portion comprises a first upstream portion having a first upstream portion inner diameter of 0.762 millimeters (0.030 inches) or smaller, and a second upstream portion, in-between the first upstream portion and the orifice, having the upstream portion inner diameter of 2.286 millimeters (0.090 inches) or larger.

5. The infusion system of claim 1 further comprising the pump, wherein the at least one sensor is disposed at the upstream portion, the orifice comprises the orifice inner diameter of 0.508 millimeters (0.020 inches) or smaller, the upstream portion comprises the first volume which is at least 25 percent smaller than the second volume of the fluid delivered by the stroke of the pump, and the upstream portion inner diameter of the upstream portion is 2.286 millimeters (0.090 inches) or larger.

6. The infusion system of claim 1 wherein the at least one sensor is disposed at the downstream portion, and the downstream portion comprises the downstream portion inner diameter of 0.508 millimeters (0.020 inches) or smaller.

7. The infusion system of claim 6 wherein the downstream portion has a length of 6.35 millimeters (0.250 inches) or longer.

8. The infusion system of claim 1 further comprising the pump, wherein the at least one sensor is disposed as the downstream portion, the upstream portion comprises the first volume which is at least 25 percent smaller than the second volume of the fluid delivered by the stroke of the pump, the downstream portion comprises the downstream portion inner diameter of 0.508 millimeters (0.020 inches) or smaller, and the downstream portion has a length of 6.35 millimeters (0.250 inches) or longer.

9. The infusion system of claim 1 wherein the at least one sensor is disposed at the upstream portion, and the cross-section of the upstream portion comprises the elliptical shape or the prolate spheroid shape in the shape of the football.

10. The infusion system of claim 9 further comprising sensors disposed at opposed corners of the elliptical shape or the prolate spheroid shape, wherein the upstream portion comprises the first volume which is at least 25 percent smaller than the second volume of fluid delivered by the stroke of the pump.

11. The infusion system of claim 10 wherein the opposed corners comprise angles of the inner passage ranging between 15 to 45 degrees.

12. An infusion system comprising:
    a pump;
    at least one sensor;
    a fluid delivery line connected to the pump for delivery fluid, the fluid delivery line comprising an inner passage extending longitudinally within the fluid delivery line, wherein the inner passage comprises:
    an upstream portion;
    a downstream portion; and
    an orifice connecting the upstream portion to the downstream portion;
    wherein: (1) the at least one sensor is disposed at the upstream portion, the orifice comprises an orifice inner diameter of 0.508 millimeters (0.020 inches) or smaller, and the upstream portion comprises a first volume which is at least 25 percent smaller than a second volume of fluid delivered by a stroke of the pump; (2) the at least one sensor is disposed at the upstream portion, the orifice comprises the orifice inner diameter of 0.508 millimeters (0.020 inches) or smaller, and an upstream portion inner diameter of the upstream portion is 2.286 millimeters (0.090 inches) or larger; (3) the at least one sensor is disposed at the downstream portion, and the downstream portion comprises a downstream portion inner diameter of 0.508 millimeters (0.020 inches) or smaller; or (4) the at least one sensor is disposed at the upstream portion, and a cross-section of the upstream portion comprises an elliptical shape or a prolate spheroid shape in the shape of a football;
    a processor in electronic communication with the pump and the at least one sensor; and
    a memory in electronic communication with the processor, wherein the memory comprises programming code for execution by the processor, and the programming code is configured to determine whether there is more than a threshold level of the air in the fluid delivery line based on measurements taken by the at least one sensor.

13. The infusion system of claim 12 wherein the at least one sensor is disposed at the upstream portion, the orifice comprises the orifice inner diameter of 0.508 millimeters (0.020 inches) or smaller, the upstream portion comprises the first volume which is at least 25 percent smaller than the second volume of the fluid delivered by the stroke of the pump, and the upstream portion inner diameter of the upstream portion is 2.286 millimeters (0.090 inches) or larger.

14. The infusion system of claim 12 wherein the at least one sensor is disposed as the downstream portion, the upstream portion comprises the first volume which is at least 25 percent smaller than the second volume of the fluid delivered by the stroke of the pump, the downstream portion comprises the downstream portion inner diameter of 0.508 millimeters (0.020 inches) or smaller, and the downstream portion has a length of 6.35 millimeters (0.250 inches) or longer.

15. The infusion system of claim 12 wherein the cross-section of the upstream portion comprises the elliptical shape or the prolate spheroid shape in the shape of the football, sensors are disposed at opposed corners of the elliptical shape or the prolate spheroid shape, the opposed corners comprise angles of the inner passage ranging between 15 to 45 degrees, and the upstream portion comprises the first volume which is at least 25 percent smaller than the second volume of fluid delivered by the stroke of the pump.

16. The infusion system of claim 12 further comprising an alarm electronically connected to the processor, wherein the processor is configured to turn on the alarm when the programming code determines that there is more than the threshold level of the air in the fluid delivery line.

17. A method for operating an infusion system comprising:
pumping fluid with a pump through a fluid delivery line, the fluid delivery line comprising an inner passage, extending longitudinally within the fluid delivery line, comprising: an upstream portion; a downstream portion; and an orifice connecting the upstream portion to the downstream portion; wherein: (1) at least one sensor is disposed at the upstream portion, the orifice comprising an orifice inner diameter of 0.508 millimeters (0.020 inches) or smaller, and the upstream portion comprising a first volume which is at least 25 percent smaller than a second volume of fluid delivered by a stroke of the pump; (2) the at least one sensor is disposed at the upstream portion, the orifice comprising the orifice inner diameter of 0.508 millimeters (0.020 inches) or smaller, and an upstream portion inner diameter of the upstream portion is 2.286 millimeters (0.090 inches) or larger; (3) the at least one sensor is disposed at the downstream portion, and the downstream portion comprises a downstream portion inner diameter of 0.508 millimeters (0.020 inches) or smaller; or (4) the at least one sensor is disposed at the upstream portion, and a cross-section of the upstream portion comprises an elliptical shape or a prolate spheroid shape in the shape of a football;
emitting and receiving signals from the at least one sensor into and from the fluid delivery line;
processing measurements of the signals, using a processor, to determine whether there is more than a threshold level of air in the fluid delivery line; and
turning on an alarm when the processor determines that there is more than the threshold level of the air in the fluid delivery line.

18. The method of claim 17 wherein the at least one sensor is disposed at the upstream portion, the orifice comprises the orifice inner diameter of 0.508 millimeters (0.020 inches) or smaller, the upstream portion comprises the first volume which is at least 25 percent smaller than the second volume of the fluid delivered by the stroke of the pump, and the upstream portion inner diameter of the upstream portion is 2.286 millimeters (0.090 inches) or larger.

19. The method of claim 17 wherein the at least one sensor is disposed as the downstream portion, the upstream portion comprises the first volume which is at least 25 percent smaller than the second volume of the fluid delivered by the stroke of the pump, the downstream portion comprises the downstream portion inner diameter of 0.508 millimeters (0.020 inches) or smaller, and the downstream portion has a length of 6.35 millimeters (0.250 inches) or longer.

20. The method of claim 17 wherein the cross-section of the upstream portion comprises the elliptical shape or the prolate spheroid shape in the shape of the football, sensors are disposed at opposed corners of the elliptical shape or the prolate spheroid shape, the opposed corners comprise angles of the inner passage ranging between 15 to 45 degrees, and the upstream portion comprises the first volume which is at least 25 percent smaller than the second volume of fluid delivered by the stroke of the pump.

* * * * *